United States Patent
Peine et al.

(10) Patent No.: US 11,925,513 B2
(45) Date of Patent: *Mar. 12, 2024

(54) CAMERA CONTROL FOR SURGICAL ROBOTIC SYSTEMS

(71) Applicant: Covidien LP, Mansfield, MA (US)

(72) Inventors: William Peine, Ashland, MA (US); Albert Dvornik, Somerville, MA (US)

(73) Assignee: COVIDIEN LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/116,466

(22) Filed: Mar. 2, 2023

(65) Prior Publication Data

US 2023/0200929 A1    Jun. 29, 2023

Related U.S. Application Data

(63) Continuation of application No. 16/643,137, filed as application No. PCT/US2018/049318 on Sep. 4, 2018, now Pat. No. 11,612,450.

(Continued)

(51) Int. Cl.
*B25J 9/10* (2006.01)
*A61B 34/37* (2016.01)
(Continued)

(52) U.S. Cl.
CPC ............ *A61B 90/361* (2016.02); *A61B 34/37* (2016.02); *A61B 90/37* (2016.02); *B25J 9/02* (2013.01); *B25J 9/10* (2013.01)

(58) Field of Classification Search
CPC .............. A61B 34/37; B25J 9/02; B25J 9/10
See application file for complete search history.

(56) References Cited

U.S. PATENT DOCUMENTS

| 5,951,461 A | 9/1999 | Nyo et al. |
| 6,926,709 B2 | 8/2005 | Bieger et al. |

(Continued)

FOREIGN PATENT DOCUMENTS

| CN | 102905641 A | 1/2013 |
| WO | 2009045827 A2 | 4/2009 |
| WO | 2016133633 A1 | 8/2016 |

OTHER PUBLICATIONS

International Search Report dated Dec. 28, 2018 and Written Opinion completed Dec. 28, 2018 corresponding to counterpart Int'l Patent Application PCT/US2018/049318.

(Continued)

*Primary Examiner* — Kira Nguyen
(74) *Attorney, Agent, or Firm* — Carter, DeLuca & Farrell, LLP

(57) ABSTRACT

Systems and methods for camera control within surgical robotic systems are provided. One system includes a computing device, multiple robot assemblies, and a surgeon console. Each robot assembly among the multiple robot assemblies includes a robotic arm. A robotic arm of a first robot assembly is coupled to an image capture device. Robotic arms of at least a subset of robot assemblies, different from the first robot assembly, are coupled to surgical instruments. The surgeon console includes multiple handles, each communicatively coupled to a robot assembly coupled to a surgical instrument. The surgeon console is configured to transmit to the computing device one or more packets that include data related to a movement of at least one handle. The computing device configured to calculate a new position of the image capture device and transmit instructions to the first robot assembly to move the image capture device to the new position.

17 Claims, 5 Drawing Sheets

Related U.S. Application Data

(60) Provisional application No. 62/554,247, filed on Sep. 5, 2017.

(51) Int. Cl.
*A61B 90/00* (2016.01)
*B25J 9/02* (2006.01)

(56) References Cited

U.S. PATENT DOCUMENTS

| | | | |
|---|---|---|---|
| 7,574,250 | B2 | 8/2009 | Niemeyer |
| 8,155,479 | B2 | 4/2012 | Hoffman et al. |
| 11,612,450 | B2 | 3/2023 | Peine et al. |
| 2002/0128552 | A1 | 9/2002 | Nowlin et al. |
| 2009/0088634 | A1 | 4/2009 | Zhao et al. |
| 2009/0326556 | A1 | 12/2009 | Diolaiti et al. |
| 2010/0161129 | A1* | 6/2010 | Costa ............... B25J 9/1697 901/47 |
| 2010/0228265 | A1* | 9/2010 | Prisco ............... B25J 9/1689 606/130 |
| 2011/0015569 | A1* | 1/2011 | Kirschenman ..... A61B 17/2909 604/95.01 |
| 2011/0040306 | A1 | 2/2011 | Prisco |
| 2011/0202068 | A1* | 8/2011 | Diolaiti ............... A61B 34/25 606/130 |
| 2012/0265071 | A1 | 10/2012 | Berke |
| 2013/0331644 | A1 | 12/2013 | Pandya et al. |
| 2014/0163736 | A1 | 6/2014 | Azizian et al. |
| 2015/0297177 | A1 | 10/2015 | Boctor et al. |
| 2016/0158938 | A1 | 6/2016 | Gombert |
| 2017/0071681 | A1* | 3/2017 | Peine ............... A61B 34/74 |
| 2017/0143429 | A1 | 5/2017 | Richmond et al. |
| 2018/0317740 | A1* | 11/2018 | Rossetto ............ A61B 1/00149 |

OTHER PUBLICATIONS

Extended European Search Report dated Apr. 30, 2021 corresponding to counterpart Patent Application EP 18855023.0.

Indian Office Action dated Mar. 23, 2022 corresponding to counterpart Patent Application IN 202017008715.

Office Action issued in Japanese Application No. 2020-513313 dated Aug. 5, 2022, together with English language translation (8 pages).

Office Action issued in corresponding Chinese Application No. 201880057442.6 dated Aug. 26, 2022, together with English language translation (27 pages).

\* cited by examiner

CAMERA CONTROL FOR SURGICAL ROBOTIC SYSTEMS

CROSS-REFERENCE TO RELATED APPLICATIONS

This application is a continuation application of U.S. patent application Ser. No. 16/643,137, filed on Feb. 28, 2020, which is a National Stage Application of PCT Application Serial No. PCT/US2018/049318 under 35 USC § 371 (a), filed on Sep. 4, 2018, which claims the benefit of and priority to U.S. Provisional Patent Application Ser. No. 62/554,247, filed on Sep. 5, 2017, the entire contents of each of the above-identified applications are hereby incorporated by reference in their entirety.

BACKGROUND

Performing surgeries using surgical robotic systems typically involves use of a camera which is inserted into the body of the patient to enable a surgeon to view a surgical site within the body of the patient. Oftentimes, when the surgical instruments are moved to a new position that lies outside an image frame provided by the camera, or even near the edge of the image frame, the surgeon needs to reposition the camera to properly capture the surgical instruments in the new position. The surgeon often needs to stop controlling the surgical instruments in order to reposition the camera, which reduces the efficiency with which the surgeon may complete the surgical procedure. Therefore, systems and devices are needed to improve camera control in surgical robotic systems and enable surgeons to perform surgeries using surgical robotic systems more efficiently.

SUMMARY

According to an aspect of the present disclosure, systems and methods are provided that address the above mentioned needs. In an aspect of the present disclosure, a surgical robotic system is provided. The system includes a computing device, multiple robot assemblies, and a surgeon console. Each robot assembly among the multiple robot assemblies includes a robotic arm. A robotic arm of a first robot assembly among the multiple robot assemblies is coupled to an image capture device. Robotic arms of at least a subset of robot assemblies, different from the first robot assembly, are coupled to surgical instruments. The surgeon console includes multiple handles, each handle among the multiple handles is communicatively coupled to a robot assembly that includes a robotic arm coupled to a surgical instrument. The surgeon console is configured to transmit to the computing device one or more packets that include data related to a movement of at least one handle among the multiple handles. The computing device is configured to calculate a new position of the image capture device and transmit instructions to the first robot assembly to move the image capture device to the new position.

In embodiments, the data related to the movement of at least one handle includes data related to a distance the at least one handle traveled and the new position of the image capture device is calculated based at least in part on data related to the distance the at least one handle traveled.

In embodiments, the new position of the image capture device is calculated based at least in part on data related to the distance the at least one handle traveled and a scaling factor applied to the distance the at least one handle traveled.

In embodiments, the scaling factor applied to the distance is among a plurality of scaling factors, each scaling factor among the plurality of scaling factors is associated with a direction of movement.

In embodiments, the system further includes the computing device configured to select the scaling factor based at least on a direction the at least one handle traveled.

In embodiments, the data related to the movement of at least one handle includes data related to a direction the at least one handle traveled and the new position of the image capture device is calculated based at least in part on data related to the direction the at least one handle traveled.

In embodiments, a direction of the new position of the image capture device relative to a current position of the image capture device is in the same direction as the direction the at least one handle traveled.

In embodiments, the computing device is further configured to calculate the new position of the image capture device in response to a determination that a velocity of the movement of the at least one handle is greater than a movement threshold value.

In embodiments, the computing device is further configured to calculate the new position of the image capture device in response to a determination that a velocity of the movement of the at least one handle is less than a sharp movement threshold value.

In embodiments, the computing device is further configured to determine if the velocity of the movement of the at least one handle is less than a sharp movement threshold value using a Kalman filter.

In embodiments, the computing device is further configured to determine if the velocity of the movement of the at least one handle is less than a sharp movement threshold value using a low pass filter.

In accordance with another aspect of the present disclosure, a surgical robotic system is provided that includes a computing device and multiple robot assemblies, with each robot assembly among the multiple robot assemblies including a robotic arm. A robotic arm of a first robot assembly among the multiple robot assemblies is coupled to an image capture device. Robotic arms of at least a subset of robot assemblies, different from the first robot assembly, are coupled to surgical instruments. The at least a subset of robot assemblies with the robotic arms coupled to the surgical instruments is configured to transmit kinematic data of the robotic arms coupled to the surgical instruments to the computing device. The computing device is configured to calculate a new position of the image capture device based at least in part on the kinematic data of the robotic arms coupled to the surgical instruments and transmit instructions to the first robot assembly to move the image capture device to the new position.

In embodiments, the computing device is further configured to identify a previous position of each of the surgical instruments coupled to the robotic arms and calculate the new position of the image capture device based at least in part on the previous position of each of the surgical instruments and the received kinematic data.

In embodiments, the computing device is further configured to calculate a change in position of each of the surgical instruments based on a previous position and a new position of each of the surgical instruments, identify a current position of the image capture device, and calculate the new position of the image capture device based at least in part on the current position of the image capture device and the change in position of each of the surgical instruments.

In accordance with another aspect of the present disclosure, a surgical robotic system is provided that includes a computing device and multiple robot assemblies, with each robot assembly among the multiple robot assemblies including a robotic arm. A robotic arm of a first robot assembly among the plurality of robot assemblies coupled to an image capture device, the image capture device is configured to capture one or more images. The first robot assembly configured to transmit the one or more captured images to the computing device. Robotic arms of at least a subset of robot assemblies, different from the first robot assembly, are coupled to surgical instruments. The computing device is configured to identify the surgical instruments within the one or more images, identify a relative point of interest based on the identified surgical instruments, calculate a new position of the image capture device based at least in part on the relative point of interest and transmit instructions to the first robot assembly to move the image capture device to the new position.

In embodiments, the relative point of interest is a centroid calculated based on locations of the surgical instruments within the one or more images.

In embodiments, the relative point of interest is a position offset from a center point calculated based on locations of the surgical instruments within the one or more images.

In embodiments, the computing device is further configured to calculate the new position of the image capture device based at least in part on a current position of the image capture device and the relative point of interest.

In embodiments, the surgical robotic system further includes a robotic arm of a second robot assembly among the multiple robot assemblies coupled to a second image capture device. The second image capture device is configured to capture one or more images that include the surgical instruments and the image capture device coupled to the first robot assembly. The second robot assembly is configured to transmit the one or more captured images to the computing device. The computing device is further configured to identify the surgical instruments and the image capture device coupled to the first robot assembly within the one or more images captured by the second image capture device, identify the relative point of interest based on the identified surgical instruments using the one or more images captured by the second image capture device, and transmit instructions to the first robot assembly to move the image capture device coupled to the first robot assembly to the new position.

In embodiments, a zoom lens of the second image capture device is positioned in a wide angle view such that an image frame of the second image capture device includes the surgical instruments and the image capture device coupled to the first robot assembly.

In embodiments, a method for camera control within a surgical robotic system is provided. The method includes receiving data related to a movement of at least one handle among multiple handles of a surgeon console. A new position of an image capture device based at least in part on the data related to the movement is calculated and instructions to a first robot assembly coupled to the image capture device are transmitted to move the image capture device to the new position.

In embodiments, the method further includes selecting the scaling factor based at least on a direction the at least one handle traveled.

In embodiments, a method for camera control within a surgical robotic system is provided. The method includes receiving kinematic data of robotic arms coupled to surgical instruments. A new position of an image capture device based at least in part on the kinematic data is calculated. Instructions are transmitted to a first robot assembly coupled to the image capture device to move the image capture device to the new position.

In embodiments, the method further includes identifying a previous position of each of the surgical instrument coupled to the robotic arms, wherein the new position of the image capture device is calculated based at least in part on the previous position of each of the surgical instruments and the received kinematic data.

In embodiments, calculating a change in position of each of the surgical instruments is based on a previous position and a new position of each of the surgical instruments. A current position of the image capture device is identified, wherein the new position of the image capture device is calculated based at least in part on the current position of the image capture device and the change in position of each of the surgical instruments.

In accordance with another aspect of the present disclosure, a method for camera control within a surgical robotic system is provided. The method includes receiving one or more images captured by an image capture device coupled to a robotic arm of a first robot assembly among a plurality of robot assemblies. Within the one or more images, surgical instruments coupled to robotic arms of at least a subset of robot assemblies among the plurality of robot assemblies, different from the first robot assembly is identified. A relative point of interest based on the identified surgical instruments is identified. A new position of the image capture device based at least in part on the relative point of interest is calculated, and instructions to the first robot assembly are transmitted to move the image capture device to the new position.

In embodiments, the method further includes receiving one or more images captured by a second image capture device coupled to a robotic arm of a second robot assembly among the plurality of robot assemblies, wherein the one or more images captured by the second image capture device include the surgical instruments and the image capture device coupled to the first robot assembly. Within the one or more images captured by the second image capture device, the surgical instruments and the image capture device coupled to the first robot assembly are identified. The relative point of interest based on the identified surgical instruments using the one or more images captured by the second image capture device is identified. The new position of the image capture device based on the relative point of interest identified using the one or more images captured by the second image capture device is calculated. Instructions to the first robot assembly are transmitted to move the image capture device coupled to the first robot assembly to the new position.

BRIEF DESCRIPTION OF THE DRAWINGS

Various aspects and features of the present disclosure are described herein below with references to the drawings, wherein.

DETAILED DESCRIPTION

Figure 1:
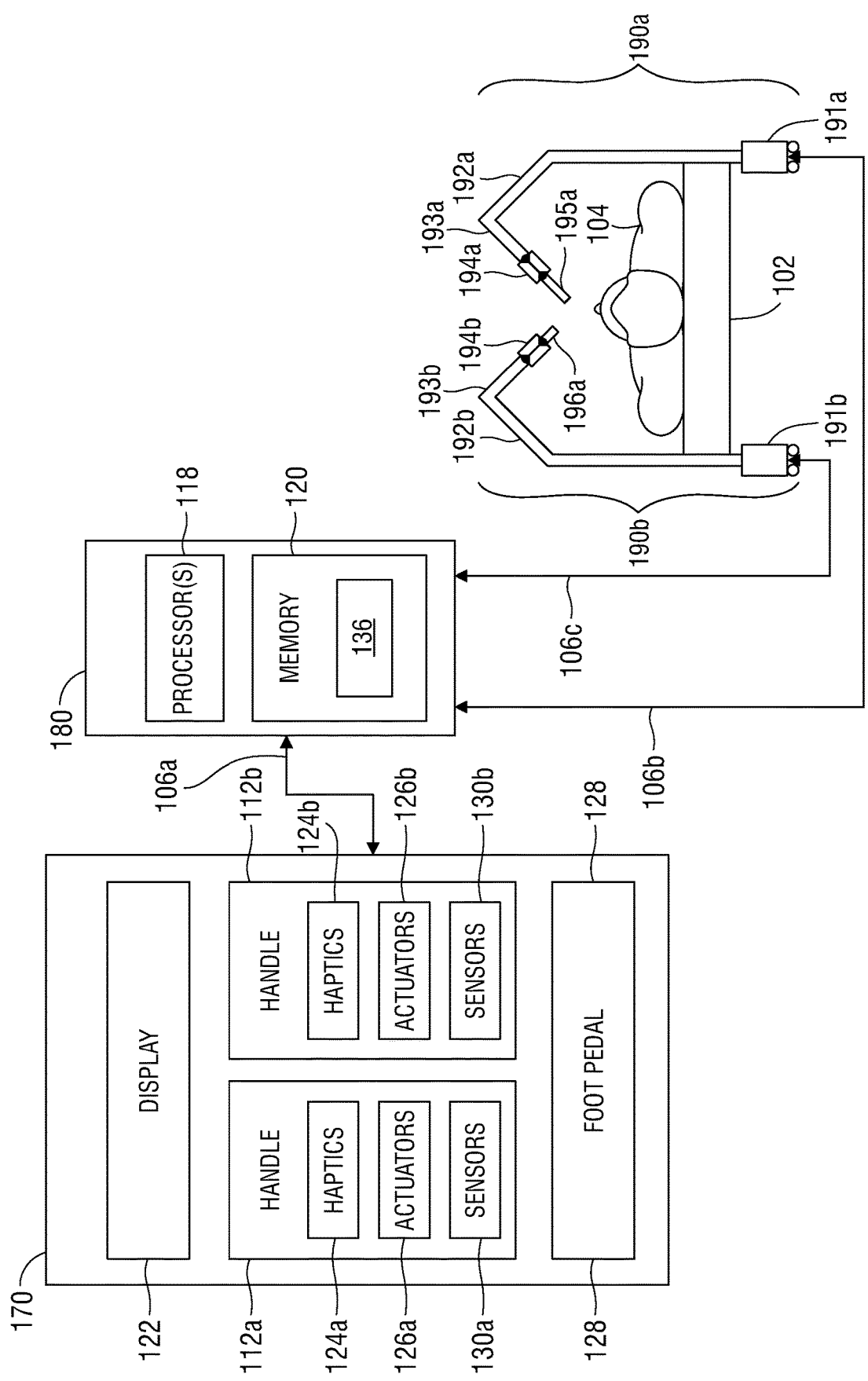
FIG. 1 illustrates an exemplary robotic surgical system, in accordance with an illustrative embodiment herein.

The present disclosure is directed to surgical robotic systems, methods, and computer-readable media for robotic surgery and improving user experience while performing surgeries using surgical robotic systems. More particularly, the present disclosure relates to systems and methods for camera control in surgical robotic systems. Specifically, the systems and methods described herein provide various techniques for concurrent control of one or more cameras of surgical robotic systems and one or more surgical instruments coupled to the surgical robotic systems while performing surgeries using the surgical robotic systems. The concurrent control of the one or more cameras and the one or more surgical instruments reduces interruptions during a surgery from performing the process of switching control from movement of only surgical instruments to movement of only the cameras, then moving the cameras to a desired location, then switching control back to the movement of only the surgical instruments from movement of the only the cameras, and then resuming the surgery. Thus, utilizing the technologies, techniques, and embodiments described herein, the surgeon is provided with an experience similar to one he or she experiences while performing a surgery where he or she has direct visual contact (for instance, visual contact without the use of a camera) of surgical instruments and the surgical site within a patient, which results in more efficient performance of surgeries using surgical robotic systems.

Embodiments of the present disclosure are now described in detail with reference to the drawings in which like reference numerals designate identical or corresponding elements in each of the several views. As used herein, the terms "user" and "clinician" refer to a doctor, a surgeon, a nurse, technician, medical assistant, or similar support personnel or any other person that may use the surgical robotic systems described herein. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring now to FIG. 1, an illustrative robotic surgical system 100 that is employed in accordance with various exemplary embodiments herein is shown. The surgical system 100 described herein is configured to operate in various operational modes including, but not limited to, concurrent control over movement of one or more cameras and surgical instruments utilized in the surgical system 100. The operational mode of the concurrent control over movement of the one or more cameras and the surgical instruments of the surgical system 100 is referred to herein, in general, as "concurrent movement control" mode. The surgical system 100 is configured to operate in multiple concurrent movement control modes, such as concurrent movement control mode based on motion of the handles (see, for example, FIG. 3), concurrent movement control mode based on kinematic data (see, for example, FIG. 4), and concurrent movement control mode based on image processing (see, for example, FIG. 5). Additional details of the concurrent movement modes are provided herein in the contexts of FIG. 2, FIG. 3, FIG. 4, and FIG. 5. The specific number of components of the system 100 depicted in FIG. 1 and the arrangement and configuration thereof are provided for illustrative purposes only, and should not be construed as limiting. For instance, various embodiments herein employ fewer or greater than all of the components shown in FIG. 1. Additionally, the system 100 depicted in FIG. 1 is provided as an illustrative context in which various exemplary embodiments herein are applicable.

The system 100 includes an operating table 102 upon which a patient 104 lies during a surgical procedure, a surgeon console 170 with which a user interacts during the surgical procedure, a computing device 180, and one or more robot assemblies, such as robot assemblies 190a, 190b, collectively referred to herein as robot assemblies 190. For convenience, the present description is made in the context of a two robot assemblies 190a, 190b, but it should be understood that the present disclosure is similarly applicable to embodiments that include more than two robot assemblies. The surgeon console 170 and the computing device 180 are communicatively coupled to one another and the robot assemblies 190a and 190b, by way of respective communication paths 106 (individually, 106a, 106b, and 106c), which, in various embodiments herein, may be implemented as wired communication paths and/or as wireless communication paths. In particular, the surgeon console 170 and the computing device 180 are communicatively coupled to one another by way of the communication path 106a. The computing device 180 and the robot assembly 190a are communicatively coupled to one another by way of the communication path 106b, and the computing device 180 and the robot assembly 190b are communicatively coupled to one another by way of the communication path 106c. The surgeon console 170 and the robot assembly 190a are communicatively coupled to one another by way of the communication path 106a, the computing device 180, and the communication path 106b. Similarly, the surgeon console 170 and the robot assembly 190b are communicatively coupled to one another by way of the communication path 106a, the computing device 180, and the communication path 106c.

The robot assembly 190a includes multiple subunits 191a, 192a, 193a, 194a. Similarly, the robot assembly 190b includes multiple subunits 191b, 192b, 193b, and 194b. Subunits 191a and 191b (collectively, 191) are cart units, subunits 192a and 192b (collectively, 192) are setup arm units, subunits 193a and 193b (collectively, 193) are robot arm units, and subunits 194a and 194b (collectively, 194) are instrument drive units. In some embodiments, a robot arm unit of a robot assembly described herein includes an instrument drive unit, such that the robot arm unit includes the subunit 193a (or 193b) and the subunit 194a (or 194b). The subunits 191a, 192a, 193a, and 194a of the robot assembly 190a are operably coupled to each other either directly or indirectly. For example, the cart unit 191a is operably coupled to the setup arm unit 192a, the robot arm unit 193a, and the instrument drive unit 194a. Similarly, the setup arm unit 192a is operably coupled to the cart unit 191a, the robot arm unit 193a, and the instrument drive unit 194a, while the robot arm unit 193a is operably coupled to the cart unit 191a, the setup arm unit 192a, the instrument drive unit 194a, and the instrument drive unit 194a is operably coupled to the cart unit 191a, the setup arm unit 192a, and the robot arm unit 193a. The subunits 191a, 192a, 193a, and 194a are also communicatively coupled to each other either directly or indirectly by way of one or more communication paths (not shown in FIG. 1). The subunits 191b, 192b, 193b, and 194b of robot assembly 190b are operably and communicatively coupled to each as subunits 191a, 192a, 193a, and 194a of robot assembly 190a.

The cart units 191a and 191b are arranged adjacent to the operating table 102 within range of the patient 104 undergoing the surgical procedure. The instrument drive units 194a and 194b are couplable to one or more corresponding surgical instruments, such as surgical instrument 195a and/or image capture devices, such as image capture device 196a that may be interchangeably fastened thereto depending on the particular surgical procedure being performed. While FIG. 1 illustrates system 100 with a single robot assembly 190a coupled to a surgical instrument 195a, system 100 may include several robot assemblies 190, each of which are coupled to a surgical instrument 195a (collectively, 195), and several robot assemblies 190, each of which are coupled to an image capture device 196a (collectively, 196). As described herein, exemplary types of image capture devices 196 include, but are not limited to, endoscopic cameras, laparoscopic cameras, any type of image capture apparatuses, or instruments coupled to image capture apparatuses. Although any type of surgical instrument 195a may be employed, example types of such surgical instruments 195 include, by way of example and not limitation, a probe, an end effector, a grasper, a knife, scissors, and/or the like. In accordance with some embodiments herein, one or more of the image capture devices 196, such as image capture device 196a, coupled to the instrument drive unit 194b is a stereoscopic image capture device included in a probe, and is inserted into the patient 104 in order to capture stereoscopic images of a region of interest inside the patient 104 during a surgical procedure. The images captured by the image capture device 196a are transmitted to the display device 122 (also referred to herein as a "display") of the surgeon console 170 that displays the images to the surgeon.

The cart units 191a and 191b are configured to move along side of the operating table 102 or the patient 104 and towards and away from the operating table 102 or the patient 104. In some embodiments, the robot assemblies of the surgical system 100, such as robot assembly 190a or 190b, include one or more drive motors (not shown in FIG. 1), which are coupled to the setup arm units 192, the robot arm units 193, and/or the instrument drive units 194 of the robot assemblies, in order to cause motion of the corresponding subunits and/or of the surgical instrument 195a or the image capture device 196a coupled thereto.

The computing device 180 includes one or more processors 118 and one or more memory units 120. The one or more processors 118 are operably coupled to the one or more memory units 120. In various embodiments, the computing device 180 may be integrated with the surgeon console 170, or may be a standalone device, such as a computing tower, disposed within or near the operating room. The one or more processors 118 may be any type of suitable processor that is adapted to perform or execute the techniques or operations or instructions described herein. For example, the processors may be hardware processors programmed to perform the techniques described herein pursuant to the instructions in firmware, memory, or other storage, or a combination thereof. Similarly, the processors may also be one or more application specific integrated circuits (ASICs), field programmable gate arrays (FPGAs) that are persistently programmed to perform the techniques or operations described herein. The processors may also be a central processing unit (CPU), a digital signal processor (DSP), a microprocessor, or any other device that incorporates hard wired logic or program logic or both to perform the operations or techniques described herein.

The one or more memory units 120 store instructions, such as instructions 136 (in an example, software), to be executed by the one or more processors 118, and the techniques described herein are performed by the computing device 180 in response to the one or more processors 118 executing the instructions stored in the one or more memory units 120. The one or more memory units 120 may be any type of hardware device used to store data. The one or more memory units 120 may be volatile memory, such as random access memory (RAM) (e.g., dynamic random access memory (DRAM), static random access memory (SRAM), and/or the like). The one or more memory units 120 may be non-volatile memory, such as read-only memory (ROM) (e.g., programmable read-only memory (EPROM), electrically erasable programmable read-only memory (EEPROM), non-volatile RAM (NVRAM), and/or the like). The one or more memory units 120 may also be magnetic, optical, or electrical media. As will be appreciated, the processor 118 and the memory units 120 implementation is provided by way of example only, and should not be construed as limiting. For instance, procedures of any of the embodiments of the present disclosure may be implemented by hardware components, firmware components, software components, and/or any combination thereof.

The surgeon console 170 includes a display device 122, handle 112A, handle 112B (collectively handles 112), with which the user interacts during a surgical procedure, and a foot pedal 128. In some embodiments, the handle 112A is a left handle and the handle 112B is a right handle, operated upon by a left hand and right hand, respectively, of the user. The display device 122 is configured to display images received by the surgeon console 170. The surgeon console 170 receives images related to the surgical site within the patient 104 from multiple image capture devices 196 including image capture device 196a and is configured to display the received images on the display device 122. In some embodiments, the display device 122 is configured to display three-dimensional (3D) images. In some embodiments, the surgeon console 170 includes a controller (not shown) configured to receive one or more stereoscopic images from one or more image capture devices 196 configured to capture stereoscopic images, such as image capture device 196a, and generate 3D images to be displayed on the display device 122. In some embodiments, the display device 122 is a touch display, or includes a touch screen, which is configured to receive inputs via a clinician's touch. During operation of the surgical system 100, the clinician moves the handles 112 of the surgeon console 170 to produce a corresponding movement and/or actuation of a setup arm unit, such as the setup arm unit 192a, a robot arm unit, such as the robot arm unit 193a, an instrument drive unit, such as the instrument drive unit 194a, and/or one or more surgical instruments 195, such as the surgical instrument 195a coupled to the instrument drive unit 194a. Based on the clinician's interrogation with the handles 112, the surgeon console 170 provides a signal and/or a message to the robot assembly 190a or 190b. In providing the signal and/or a message to the robot assembly 190a or 190b, the surgeon console 170 transmits the signal and/or message to the computing device 180 by way of the communication path 106a. The computing device 180 transmits the signal and/or message to robot assembly 190a by way of the communication path 106b and/or to robot assembly 190b by way of the communication path 106c. In some embodiments, the signal and/or the message is transmitted to the cart unit 191a or the cart unit 191b of the robot assemblies 190a or 190b, respectively, which provide, by way of other communication paths (not shown in FIG. 1), corresponding signals or instructions to the subunits of the respective robot assemblies in order to cause the performance of commanded action.

The surgeon console 170 includes sensors 130A and 130B (collectively, sensors 130) that are configured to determine metrics related to the motions of the handle 112A and the handle 112B, respectively. Exemplary types of the metrics related to the motions of the handles 112 include, but are not limited to, the direction of the motion of the handles 112, the velocity of the motion of the handles 112, the distance of movement of the handles 112, the force of the motion of the handles 112, the torque of the motion of the handles 112, and/or the like. The surgeon console 170 transmits the metrics data related to the motions of the handles 112 to computing device 180 and/or robot assemblies of the surgical system 100, such as robot assembly 190a and robot assembly 190b.

The handle 112A, in some embodiments, includes various haptics 124A and/or actuators 126A, which provide feedback to the surgeon relating to various tissue parameters or conditions, such as, tissue resistance due to manipulation, cutting, or otherwise treating, pressure by the instrument onto the tissue, tissue temperature, tissue impedance, and/or the like. Similarly, the handle 112B, in some embodiments, includes various haptics 124B and/or actuators 126B, which are configured similar to as haptics 124A and/or actuators 126A. The haptics 124A and 124B are referred to herein collectively as haptics 124. The actuators 126A and 126B are referred to herein as collectively as the actuators 126. As can be appreciated, such haptics 124 provide the surgeon with enhanced feedback, such as kinesthetic feedback (for example, gross force feedback, gross motion feedback, and/or the like) that may be sensed through the muscles and joints and/or tactile feedback (for example, vibration feedback, temperature feedback, small-scale shape feedback, and/or the like) that may be sensed through mechanoreceptors in the skin, thereby simulating actual operating conditions. The haptics 124 may include vibratory motors, electroactive polymers, piezoelectric devices, electrostatic devices, subsonic audio wave surface actuation devices, reverse-electrovibration, or any other device capable of providing a tactile feedback to a user. As mentioned above, the handles 112 may also include a variety of different actuators 126, which, for instance, may be employed for delicate tissue manipulation and/or treatment further enhancing the surgeon's ability to mimic actual operating conditions. In some embodiments, one or more motors (not separately shown in FIG. 1) drive the haptics 124 and/or the actuators 126 to provide kinesthetic force feedback, for instance, indicating one or more tissue properties, indicating a range of motion of the surgical instrument 195a, and/or indicating that a tracking error has become large, which may be due to a collision or another motion impediment.

The foot pedal 128 is configured to receive one or more inputs from a clinician to the surgeon console 170. Exemplary types of the inputs to the surgeon console 170 from the foot pedal 128 include, but are not limited to, inputs for activating and deactivating one or more operational modes of the surgical system 100, including the concurrent movement control mode. The foot pedal 128 is configured to be placed into two or more positions and a position of the foot pedal 128 is associated with an input to the surgeon console 170. The selection of a position of the foot pedal 128 provides the associated input to the surgeon console 170. For example, if a first position of the foot pedal 128 is associated with activating an operational mode of the surgical system 100 and a second position of the foot pedal 128 is associated with deactivating the operational mode of the surgical system 100, then selection of the first position provides an input to the surgeon console 170 to activate the operational mode and selection of the second position provides an input to the surgeon console 170 to deactivate the operational mode. One of the positions of the foot pedal 128 is configured to be a rest position of the foot pedal 128. An input signal is not transmitted to the surgeon console 170 when the foot pedal 128 is in the rest position. In some embodiments, when the foot pedal 128 is in the rest position, an input is transmitted to the surgeon console 170 indicating that the foot pedal 128 is not being interrogated with by a user. In some embodiments, the foot pedal 128 is a momentary foot pedal switch and inputs to the surgeon console 170 are transmitted based on a sequence of interrogations with the foot pedal 128, such as double tapping the foot pedal 128.

The surgeon console 170 is configured to determine one or more operations to be performed based on the inputs received via the foot pedal 128. The surgeon console 170 transmits the inputs received via the foot pedal 128 to the computing device 180 and/or the robot assemblies of the surgical system 100. The surgeon console 170 is also configured to determine whether an operational mode of the surgical system 100 is selected based on the inputs received via the foot pedal 128, and then determine one or more operations associated with the selected operational mode to be performed based on the inputs received via the foot pedal 128.

In some embodiments, the foot pedal 128 is operably and/or communicatively coupled to the computing device 180 and, in response to receiving an input from a user, such as selection of a position of the foot pedal 128, the foot pedal 128 transmits an input signal associated with the selected position directly to the computing device 180. The computing device 180 is configured to determine one or more operations, including activating or deactivating operational modes of the surgical system 100, to be performed based on the input signals received from the foot pedal 128. In some embodiments, the computing device 180 transmits messages or packets to the surgeon console 170 that include data that identify the inputs received from the users via the foot pedal 128.

As described above, the components of the system 100, such as surgeon console 170, the computing device 180, the robot assemblies 190, and/or the like, are configured to receive data from and transmit data to one another. In some embodiments, the data received and transmitted by the components of the system 100 is associated with an identifier that indicates the type of the data. As used herein in this context, the term "type of data" generally refers to a category of information to which data is related. Each type of data is associated with a unique identifier, referred to herein as "data type identifier." For example, data related to motion of the handles 112 of the surgeon console 170 is associated with a data type identifier, while data providing a confirmation is associated with another data type identifier. The components of the system 100 are configured to transmit the data type identifier associated with data to the component receiving the data. The components of the system 100 are configured to determine the type of data received by the components based on the data type identifier associated with the received data. The components of the system 100 are configured with a set of rules that associate types of data with corresponding data type identifiers, referred to herein as "data type rules."

The components of the system 100 are configured to identify a data type identifier associated with a type of data, based on the data type rules. For example, the surgeon console 170 is configured to identify a data type identifier corresponding to data related to the motion of the handles 112 based on the data type rules, and associate the data related to the motion of the handles 112 with the corresponding data type identifier and transmit the associated data type identifier to the component of the system 100 that received the data related to the motion of the handles 112, such as the computing device 180. The component that received the data related to the motion of the handles 112, such as the computing device 180, is configured to determine the type of the received data based on the data type rules, and the data type identifier received by the component and associated with the received data. In some embodiments, the components of the system 100 are configured to transmit data to and receive data from one another in one or more packets. In some embodiments, the component of the system 100 transmitting data in one or more packets includes the data type identifier associated with the data in at least one of the one or more packets transmitted.

Figure 2:
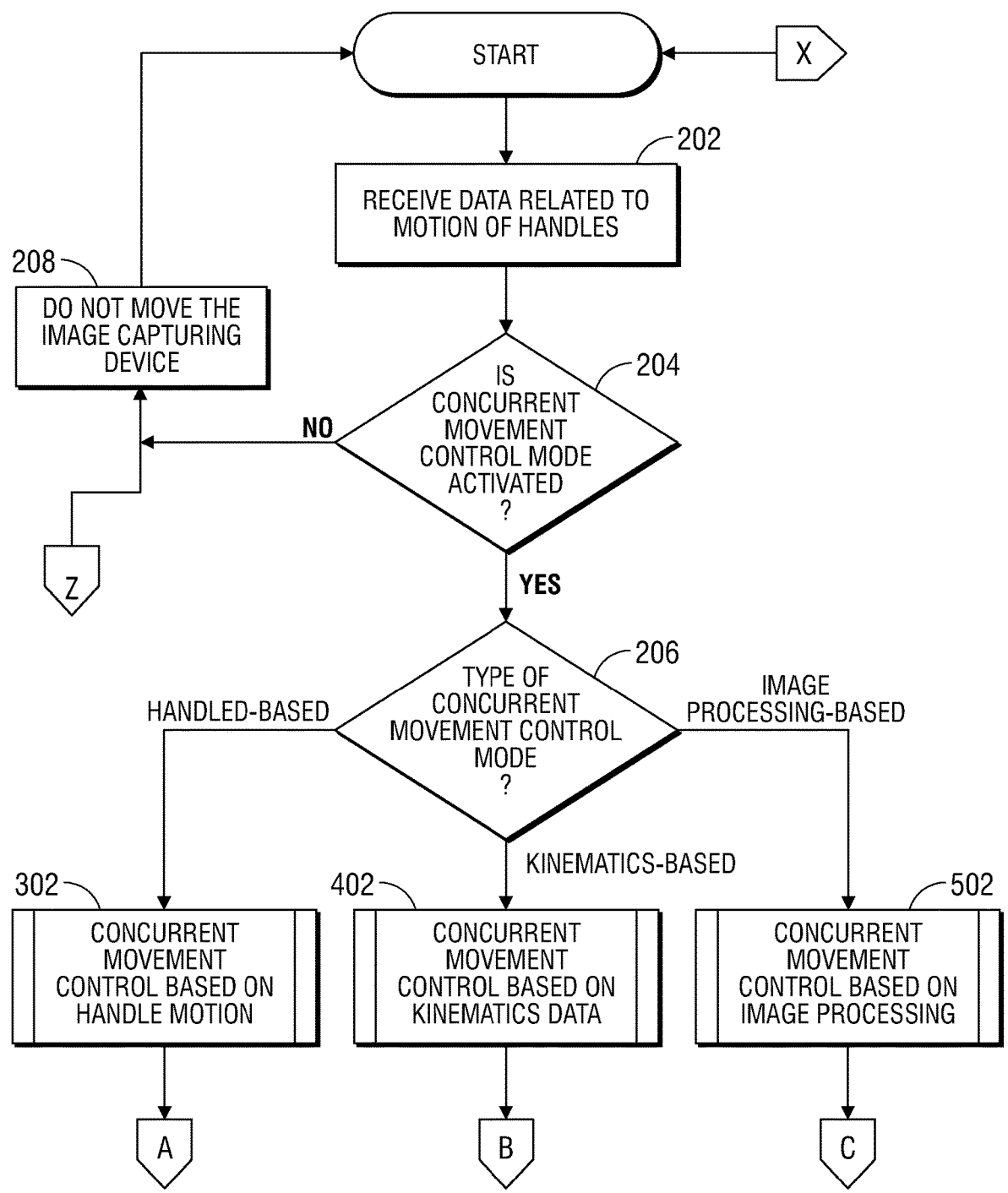
FIG. 2 is a flowchart that illustrates an exemplary method of employing the surgical robotic system of FIG. 1 to determine whether any type of concurrent movement control mode is activated.

Turning now to FIG. 2, an illustrative method 200 of determining whether concurrent movement control mode is activated and identifying the activated type of concurrent movement control mode is shown. A user activates concurrent movement control mode of the surgical system 100 by providing an input that indicates that the user desires that the concurrent movement control mode of the surgical system 100 be enabled. An example of providing such an input by a user is by the user selecting a corresponding position on the foot pedal 128, thereby causing the surgeon console 170 to transmit data to the computing device 180 instructing the computing device 180 to activate the concurrent movement control mode. In embodiments where the foot pedal 128 is operably and/or communicatively coupled directly to the computing device 180, the computing device 180 directly receives an input signal from the foot pedal 128 that indicates that the user desires to activate the concurrent movement control mode of the surgical system 100 and the computing device 180 transmits data to the surgeon console 170 that the user desires to activate the concurrent movement control mode of the surgical system 100.

Another example of a user providing an input that indicates that the user desires that the concurrent movement control mode of the surgical system 100 be activated is via a selection of one or more graphical items on a graphical user interface (GUI) presented to the user. The surgeon console 170 is configured to present such a GUI (not shown in FIG. 2) on the display device 122. The GUI displayed on the display device 122 presents one or more graphical items that are configured to receive inputs to the surgeon console 170 for activating or deactivating various operational modes of the surgical system 100, including, but not limited to, the concurrent movement control mode. The surgeon console 170, in response to receiving an input via the GUI to activate the concurrent movement control mode, transmits data to activate the concurrent movement control mode to the computing device 180. In some embodiments, the surgeon console 170 is configured to process speech and receive inputs orally from a user and output prompts or requests orally to the user and an input to the surgeon console 170 to activate the concurrent movement control mode is provided orally. With the activation of a concurrent movement control mode, the handles 112 of the surgeon console 170 are not disconnected from controlling movements of the surgical instruments 195, such as surgical instrument 195*a*. Furthermore, with the activation of the concurrent movement control mode, the handle 112A and the handle 112B are not locked together, but remain independent of each other such that a user may move handle 112A and handle 112B independently of each other.

In step 202, the computing device 180 receives data related to the motion of the handles 112 of the surgeon console 170. The data related to the motion of the handles 112 of the surgeon console 170 is data based on the user's input to the surgeon console 170, via the handles 112, to move one or more surgical instruments 195 coupled to the robot assemblies of the system 100, such as the robot assemblies 190. In some embodiments, the data received by the computing device 180 includes metrics data related to the motion of the handles 112, such as distance, direction, velocity, and/or the like, of the motion of the handles 112. In step 204, the computing device 180 determines whether the concurrent movement control mode is activated. In response to determining that the concurrent movement control mode is not activated ("NO" at step 204), then in step 208, the computing device 180 does not move the one or more image capture devices 196, such as image capture device 196*a* coupled to the robot assemblies of the surgical system 100, such as robot assembly 190*b*.

In response to determining that the concurrent control mode is activated ("YES" at step 204), then in step 206, the computing device 180 determines the type of concurrent movement control mode that is activated. After a user provides an input to activate concurrent movement control mode, the user is prompted to specify the type of concurrent movement control mode that the user desires to activate. In some embodiments the user is prompted to specify the type of concurrent movement control mode via a graphical prompt item is displayed on the GUI presented on the display 122. The graphical prompt item displays the various types of concurrent movement control mode in which the surgical system 100 is configured to operate and requests the user to select one of the types of concurrent movement control mode. In embodiments where the surgeon console 170 is configured to process speech and receive inputs orally from a user, the surgeon console outputs prompts or requests orally to specify the type of concurrent movement control mode. For example, the surgeon console 170, in response to receiving an oral input from a user to activate the concurrent movement control mode, outputs a prompt to the user to state the type of concurrent movement control mode to activate. In embodiments where the foot pedal 128 is operably and/or communicatively coupled directly to the computing device 180, the computing device 180 transmits data to the surgeon console 170 to request the user to specify the type of concurrent movement control mode.

In some embodiments, the surgeon console 170 includes one or more input devices (not shown), such as handles, switches, knobs, joysticks and/or the like, and each position of the input device is associated with a type of concurrent movement control mode and selection of a position of the input device transmits a corresponding signal to the surgeon console 170. For example, if the surgeon console 170 is configured with a knob with multiple positions and a first position of the knob is associated with concurrent movement control mode based on movement of the handles 112, a second position is associated with concurrent movement control mode based on kinematics data of robot arm units of robot assemblies that are coupled to surgical instruments, and a third position is associated with concurrent movement control mode based on image processing, then the selection of the third position of the knob provides an input to the surgeon console 170 that the concurrent movement control mode based on image processing is selected.

In response to receiving data that indicates the type of concurrent movement control mode selected by the user, the computing device 180 activates the type of concurrent movement control mode of the surgical system 100 by storing data that indicates that the selected type of concurrent movement control mode is activated, and in response to receiving data related to movement of handles 112 from the surgeon console 170, the computing device 180 is configured to check the stored data to determine whether one or more image capture devices 196 of the surgical system 100 should be moved. In some embodiments, the computing device 180 is configured with default type of concurrent movement control mode and in response to receiving an input that the user desires to activate the concurrent movement control mode, the computing device 180 activates the default type of concurrent movement control mode by storing data that indicates that the default type of concurrent movement control mode activated. In some embodiments, a user is presented with options to change the activated type of concurrent movement control mode and, in response to selection of an option, the computing device 180 deactivates the activated type of concurrent movement control mode and activates the new type of concurrent movement control mode. For example, if default type of concurrent movement control mode is concurrent movement control mode based on motion of handles 112 of the surgeon console 170, and the user provides an input to activate concurrent movement control mode of the surgical system 100, then the computing device 180 activates the default type of concurrent movement control mode and transmits data to the surgeon console 170 to present options of the other types of concurrent movement control mode to the user via the GUI displayed on the display 122. In response to the selection of an option displayed on the GUI, the computing device 180 deactivates the activated concurrent movement control mode (concurrent movement control mode based on motion of handles 112 of the surgeon console 170) and activates the concurrent movement control mode associated with the selected option.

Figure 3:
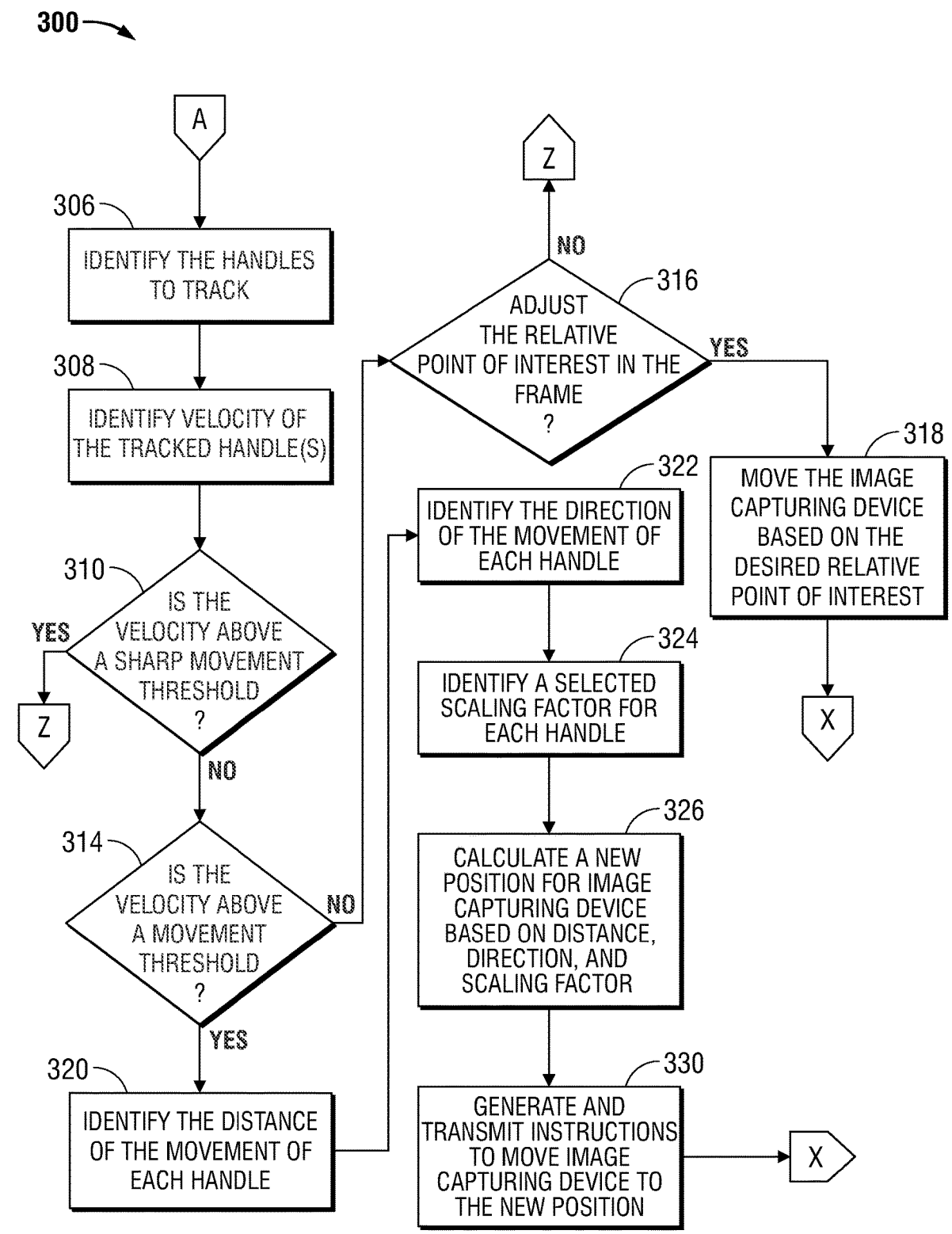
FIG. 3 is a flowchart that illustrates an exemplary method of employing the surgical robotic system of FIG. 1 to move the camera based on motions of the handles of the surgical console.

In step 206, in response to determining that the type of concurrent movement control mode is based on motion of a handle 112 of the surgeon console 170 of the surgical system 100 ("HANDLE-BASED" at step 206), the computing device 180 performs sub-process 302, additional details of which are provided herein in the context of FIG. 3. In response to determining that the type of concurrent movement control mode is based on kinematic data ("KINEMATICS-BASED" at step 206), the computing device 180 performs sub-process 402, additional details of which are provided herein in the context of FIG. 4. In response to determining that the type of concurrent movement control mode is based on image processing ("IMAGE PROCESSING-BASED" at step 206), the computing device 180 performs sub-process 502, additional details of which are provided herein in the context of FIG. 5.

Turning now to FIG. 3, an illustrative method 300 for moving an image capture device 196 in concurrent movement control mode based on the motion of a handle 112 of the surgeon console 170 of the surgical system 100 is shown.

In step 306, the computing device 180, identifies the handles 112 of the surgeon console 170 that are to be tracked. As described above, the settings associated with the concurrent movement control mode based on the motion of a handle 112 are transmitted to the computing device 180 and the computing device 180 stores the settings in a data storage unit operably coupled to the computing device 180. One of the settings associated with the concurrent movement control mode based on the motion of a handle 112, specifies the handles 112 to track. For example, the settings may indicate that only one of the handles 112, such as the handle 112A, is to be tracked. Similarly, the settings may indicate that all handles 112 are to be tracked. The computing device 180 identifies the handles 112 to track based on the settings data associated with the activated concurrent movement control mode.

The computing device 180 is configured to prevent translation of unintentional movements of the handles 112 of the surgeon console 170 into movements of the one or more image capture devices 196, such as image capture device 196a. By preventing the translation of unintentional movements of the handles 112, the computing device 180 eliminates any further steps or inputs from the user to reposition the image capture devices 196 back into their positions prior to the unintentional movements of the handles 112. Thus, the computing device 180 efficiently eliminates unintended movements of the image capture devices 196 and prevents unsteady images of the surgical site due to the abrupt motions of the handles 112. Examples of these techniques are shown in steps 308 and 310. In step 308, the computing device 180 identifies the velocity of motion of each of the identified handles 112. In step 310, the computing device 180 determines whether velocity of the identified handles 112 is above a sharp movement threshold value. As used herein, the term "sharp movement threshold value" corresponds to a value of a velocity of a handle 112 when moved is significantly greater than the expected velocity of the handle 112 when moved during a surgical procedure. In some embodiments, the sharp movement threshold value is specified in configuration data stored in one or more memory of the computing device 180 or in a storage unit operably coupled to the computing device 180, and the computing device 180 is configured to retrieve the sharp movement threshold value from memory or data storage unit in determining whether velocity of the identified handles 112 is above the sharp movement threshold value.

If the computing device 180 determines that the velocity of any of the identified handles 112 is above the sharp movement threshold value ("YES" at step 310), then the computing device 180 identifies the movement of the handle 112 as unintentional and returns process to the step 208 in FIG. 2. The computing device 180 does not transmit instructions to one or more robot assemblies of system 100 that are coupled to the one or more image capture devices 196, such as the robot assembly 190b, to move the one or more image capture devices 196. In some embodiments, the computing device 180 is configured to apply a low pass filter or Kalman filter to the data related to the motion of the handles 112 in order to filter out velocities of the identified handles 112 above the sharp movement threshold value. In some embodiments, the computing device 180 transmits a message to the surgeon console 170 indicating that the movement of the handle 112 has been determined to be an unintentional movement and that the one or more image capture devices 196 coupled to the robot assemblies 190 will not be moved. In some embodiments, the surgeon console 170 displays an alert message on the GUI that indicates that the one or more image capture devices 196 coupled to the robot assemblies 190 were not moved because the speed of the handle 112 exceeded a safety threshold.

If the computing device 180 determines that the velocity of each identified handle 112 is not above the sharp movement threshold ("NO" at step 310), then in step 314, the computing device 180 determines whether the velocity of each identified handle 112 is above a movement threshold value. As used herein, the term "movement threshold value" refers to a value that indicates the minimum velocity of the handle 112 necessary to determine a movement of the handle 112 as a deliberate and an intended movement by the user. In some embodiments, similar to the sharp movement threshold value, the movement threshold value is specified in configuration data stored in memory of the computing device 180 or in a storage unit operably coupled to the computing device 180, and the computing device 180 is configured to retrieve the movement threshold value from memory or data storage unit in determining whether velocity of the identified handles 112 is above the movement threshold value.

In some embodiments, filtering is applied to the velocity of the identified handles 112 to implement a backlash-type feature, which operates as follows. The handle(s) 112 must move far enough in one direction in order for the image capture device 196 to begin to move in a corresponding direction. The image capture device 196 will continue to move, within limits, in the corresponding direction, so long as the handle(s) 112 continues moving in a generally similar direction. If the handle(s) 112 reverses direction, the handle(s) 112 must move through a dead zone before the image capture device 196 will begin to track the handle motion in the new (reversed) direction. In this manner, the surgeon can move the handles 112 around within the dead zone without causing a corresponding motion of the image capture device 196, and then can move the handles 112 beyond the dead zone to cause the image capture device 196 to track in the corresponding direction and drag the dead zone along in a similar direction.

If the computing device 180 determines that the velocity of any of the identified handles 112 is not above the movement threshold value ("NO" at step 314), then in step 316, the computing device 180 determines whether the relative point of interest in the image frame should be adjusted. As used herein, the term "relative point of interest in an image frame" refers to particular position or point in an image frame relative to one or more surgical instruments 195 coupled to the robot assemblies of system 100, for example, a center point of the tip of a surgical tool, a center point between two or more surgical tool tips, a centroid of two or more surgical tool tips, a position that is offset from the center point or centroid of two or more surgical tool tips, and/or the like.

In determining whether the relative point of interest in the image frame should be adjusted, the computing device 180 calculates a new relative point of interest in the image frame based on changes to the positions of the surgical tool tips and then determines if the distance between the new and the previous relative point of interest in the image frame is greater than a threshold value. If the computing device 180 determines that the distance is not greater than the threshold value ("NO" at step 316), then the computing device 180 returns the process to step 208 in FIG. 2, and does not transmit instructions to the robot assemblies to move the image capture devices 196. If the computing device 180 determines that the distance is greater than the threshold value ("YES" at step 316), then in step 318, the computing device 180 generates instructions to move the image capture device 196 to the new relative point of interest in the image frame. In some embodiments, the new relative point of interest in the image frame is calculated based on the distance and the angle in which the tips of the surgical tools are moved.

If the computing device 180 determines that the velocity of each of the identified handles 112 is above the movement threshold value ("YES" at step 314), then in step 320, the computing device 180 identifies the distance of the movement of each of the identified handles 112. In some embodiments, the computing device 180 receives data related to the distance of the movement of each the identified handles 112. For example, the distance of the movement of each of the identified handles 112 is received in the one or more packets corresponding to the data related to the movements of the identified handles 112. If more than one handle among the handles 112 is identified, then the computing device 180 identifies the distance of the movement of the identified handles 112 by calculating a statistical measurement, such as an average, based on the distance of movement of each of the identified handles 112. For example, if two handles among the handles 112 are identified as handles 112 to track and one handle is moved 10 centimeters (in a single direction) while the other handle is moved 15 centimeters (in the same single direction) and an average is selected as the statistical measurement to calculate, then the computing device 180 calculates an average distance that the handles 112 combined moved, 12.5 centimeters, and identifies 12.5 centimeters as the distance of the movement of the identified handles 112.

In step 322, the computing device 180 identifies the direction of the movement of the identified handles 112. As described above, the handles 112 of the surgeon console 170 are configured to move in various directions including, but not limited to, left, right, up, and/or down, and/or in a manner that causes the image capture device 196 to zoom in or zoom out. In some embodiments, the computing device 180 receives data related to the direction of the movement of the identified handles 112 in the one or more packets corresponding to the data related to the movements of the identified handles 112. In some embodiments, the data related to the direction of the movement of the identified handle 112 is specified in as a value in range between zero to 359 degrees.

In step 324, the computing device 180 identifies a scaling factor for each of the identified handles 112. As used herein, the term "scaling factor" refers to a ratio between a movement of a handle 112 to a movement a surgical instrument coupled to a robot assembly. For example, a scaling factor is 3:1 indicates that a movement of a handle 112 by three inches translates to a movement of a surgical tool coupled to a robotic assembly by 1 inch. Similarly, a scaling factor of 2:1 indicates that movement of a handle 112 by two inches translates to a movement of a surgical tool coupled to a robotic assembly by 1 inch, and a scaling factor of 5:1 indicates that movement of a handle 112 by five inches translates to a movement of a surgical tool coupled to a robotic assembly by 1 inch. The scaling factors for the system 100 may be selected in any one or more ways including, but not limited to, selecting the scaling factor via the GUI displayed on display 122 of the surgeon console 170, via an analog input mechanism, such as a knob, by selecting a position of the foot pedal 128 during or after activation of concurrent movement control mode. For example, if the concurrent movement control mode is activated and a first position of the foot pedal 128 is associated with increasing a scaling factor to translate the movement of the handles 112 to the movement of an image capture device 196 and a second position of the foot pedal 128 is associated with decreasing the scaling factor to translate the movement of the handles 112 to the movement of the image capture device 196, then selection of the first position increases the scaling factor and the selection of the second position decreases the scaling factor.

The system 100 is configured to allow selection of multiple scaling factors for a particular operating mode, such as one of the concurrent movement control operating modes. Each scaling factor is associated with a different direction of movement of the handles 112 of the surgeon console 170, and/or with a different position of a lens of an image capture device 196, such as image capture device 196a, coupled to a robot assembly of the system 100, such as robot assembly 190b. The scaling factors are specified within configuration data stored in memory of computing device 180 or a data storage unit operably coupled to the computing device 180 and the computing device 180 is configured to identify a scaling factor of a handle 112 based on the identified direction of the movement of the handle 112 or the position of the lens of the image capture device 196 relative to the surgical instruments 195. For example, if scaling factor of 3:1 is associated with the movement of a handle 112 to the left and a scaling factor of 2:1 is associated with the movement of a handle 112 to the right, then the computing device 180 selects a scaling factor of 3:1 for the handle 112 that is moved left and a scaling factor of 2:1 for the handle 112 that moved to the right. Similarly, if, for example, the lens of the image capture device 196 is in a position that corresponds to the lens being zoomed out, then the computing device 180 determines whether the lens is in a zoomed out position and, in response to determining that the lens is in a zoomed out position, identifies the scaling factor specified for the lens in a zoomed out position. In some embodiments, if each handle 112 is moved in the same direction then a single scaling factor is applied to each of the handles 112. For example, if the handle 112A and the handle 112B are moved to the left, then the scaling factor associated with the left direction is applied to both the handles 112A and 112B.

In step 326, the computing device 180 calculates a new position for the image capture device 196 based on the identified distances, directions and scaling factor. The computing device 180 calculates the new position of the image capture device 196, by calculating a scaled distance of movement of each identified handle 112 by applying the corresponding scaling factor of that handle 112 to the identified distance of movement of that handle 112 and, by calculating a final distance and direction of movement of the image capture device 196 based on a mathematical function that accepts as inputs the scaled distance of movement of each of the identified handles 112 and the direction of movement of each of the identified handle 112. An example of a mathematical function that accepts as inputs the scaled distance of movement of each of the identified handles 112 and the direction of movement of each of the identified handle 112 is an averaging function that accepts as inputs, vectors with magnitudes and direction. For example, if two handles among the handles 112 are identified and if one of the identified handles 112 is moved 10 cm to the right (i.e., direction of movement is zero degrees) and the other of the identified handles 112 is moved 15 cm to the left (i.e., direction of movement is 180 degrees) and the scaling factor is 5:1 and the mathematical function is an averaging function, then the scaled distance is 2 cm to the right and 3 cm to the left and applying the averaging function to the scaled distances and their respective directions results in a final distance and direction of movement of the image capture device 196 of 0.5 cm to the left (or 180 degrees). Therefore, the new position of the image capture device 196 is 0.5 cm to the left (or 180 degrees) of the current position of the image capture device 196.

In step 330, the computing device 180 generates and transmits to the robot assembly 190 coupled to the image capture device 196 instructions to move the image capture device 196 to the new position. In some embodiments, the computing device 180 identifies a unique identifier associated with the robot assembly coupled to the image capture device 196 and generates and transmits instructions to the robot assembly using the unique identifier. As noted above in connection with steps 204 and 208, if concurrent movement control mode is not activated ("NO" at step 204), for instance during a period in which the image capture device 196 is clutched out or in a hold mode, then the image capture device 196 does not track the movement of the handles 112.

Figure 4:
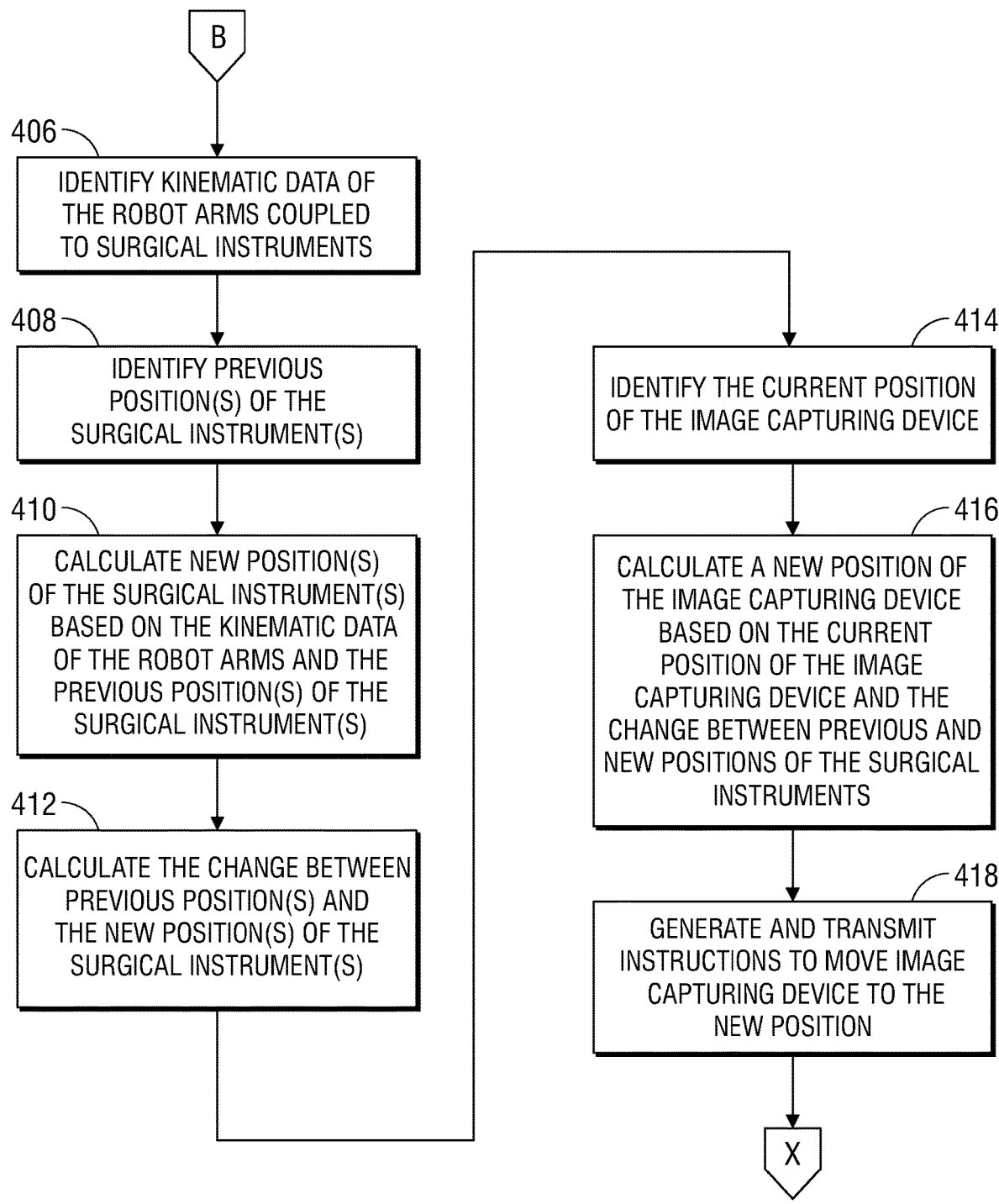
FIG. 4 is a flowchart that illustrates an exemplary method of employing the surgical robotic system of FIG. 1 to move the camera based on kinematic data.

Turning now to FIG. 4, an illustrative method 400 for moving an image capture device 196 in concurrent movement control mode based on kinematics data of robot arms 193 coupled to surgical instruments 195 of the robot assemblies of the surgical system 100 is shown. As used herein, the term "kinematics data" refers to data related to positions and/or orientations of setup arm units 192, robot arm units 193, instrument drive units 194, and/or other joints of robot assemblies 190. The computing device 180 in step 406, identifies kinematic data of the robot arms 193 coupled to the surgical instruments 195, such as the surgical instrument 195a. The robot assemblies 190 include encoders that are configured to output kinematic data of the robot arm, such as the robot arm 193a. The kinematic data includes data related to movement of the robot arm 193a to the left, right, up, down, movement of the arm towards the patient, away from the patient, degree of rotation of the arm. The kinematic data of the robot arms 193 is transmitted to the computing device 180 from the robot assemblies 190 whose robot arms 193 are coupled to surgical instruments 195, such as surgical instrument 195a, that are moved. In some embodiments, the computing device 180 is configured to identify the kinematic data of the robot arms coupled to the surgical instruments 195, such as robot arm 193a coupled to surgical instrument 195a, based on the commands or instructions transmitted to the robot assemblies to move their robot arms.

In step 408, the computing device 180 identifies previous positions of the surgical instruments 195, such as surgical instrument 195a. The positions of the surgical instruments 195 are represented in a three-dimensional coordinate system, represented by a coordinate system in x, y, and z directions. The computing device 180 is configured to save the previous positions of the surgical instruments 195 in a memory of the computing device 180 or a data storage unit operably coupled to the computing device 180. In some embodiments, the computing device 180 receives positions of the surgical instruments 195 from the robot assemblies coupled to surgical instruments 195 and is configured to store the received positions of the surgical instruments 195 in a memory of the computing device 180 or a data storage unit operably coupled to the computing device 180. In step 410, the computing device 180 calculates a new position for each of the surgical instruments 195 associated with the one or more handles 112 that are moved based on the identified kinematic data of the robot arms coupled to surgical instruments 195 and the previous positions of the surgical instruments 195.

In step 412, the computing device 180 calculates a change in position between the previous position and the new position of each surgical instrument. The change in position is calculated in a three-dimensional coordinate space with points in x, y, and z directions. In step 414, the computing device 180 identifies the current position of the image capture device 196. In some embodiments, the computing device 180 receives the position of the image capture device 196 from the robot assembly coupled to the image capture device 196 after the image capture device 196 is moved, and the computing device 180 stores the position in a memory of the computing device 180 or data storage unit operable coupled to the computing device 180. In some embodiments, the computing device 180 receives kinematic data of the robot arm coupled to the image capture device 196 from the robot assembly 190 after the image capture device 196 is moved and the computing device 180 is configured to calculate the position of the image capture device 196 based on the received kinematic data and to store the calculated position of the image capture device 196 in a memory of the computing device 180 or data storage unit operably coupled to the computing device 180.

In step 416, the computing device 180 calculates a new position of the image capture device 196 based on the identified current position of the image capture device 196 and the change in position between previous and new positions of the surgical instruments 195. In step 418, the computing device 180 generates and transmits instructions to move the image capture device 196 to the new position to the robot assembly coupled to the image capture device 196. In some embodiments, various additional features may be applied to the kinematic data-based concurrent movement control mode that is described in connection with FIG. 4 in a manner similar to that described herein in connection with FIG. 3 for the handle motion-based concurrent movement control mode. Exemplary types of such features include, without limitation, filtering, velocity limiting, backlash/dead zone functionality, and/or the tying of motion of the image capture device 196 to a position of the handle 112 and/or to a mathematical combination of respective positions of multiple handles 112.

Figure 5:
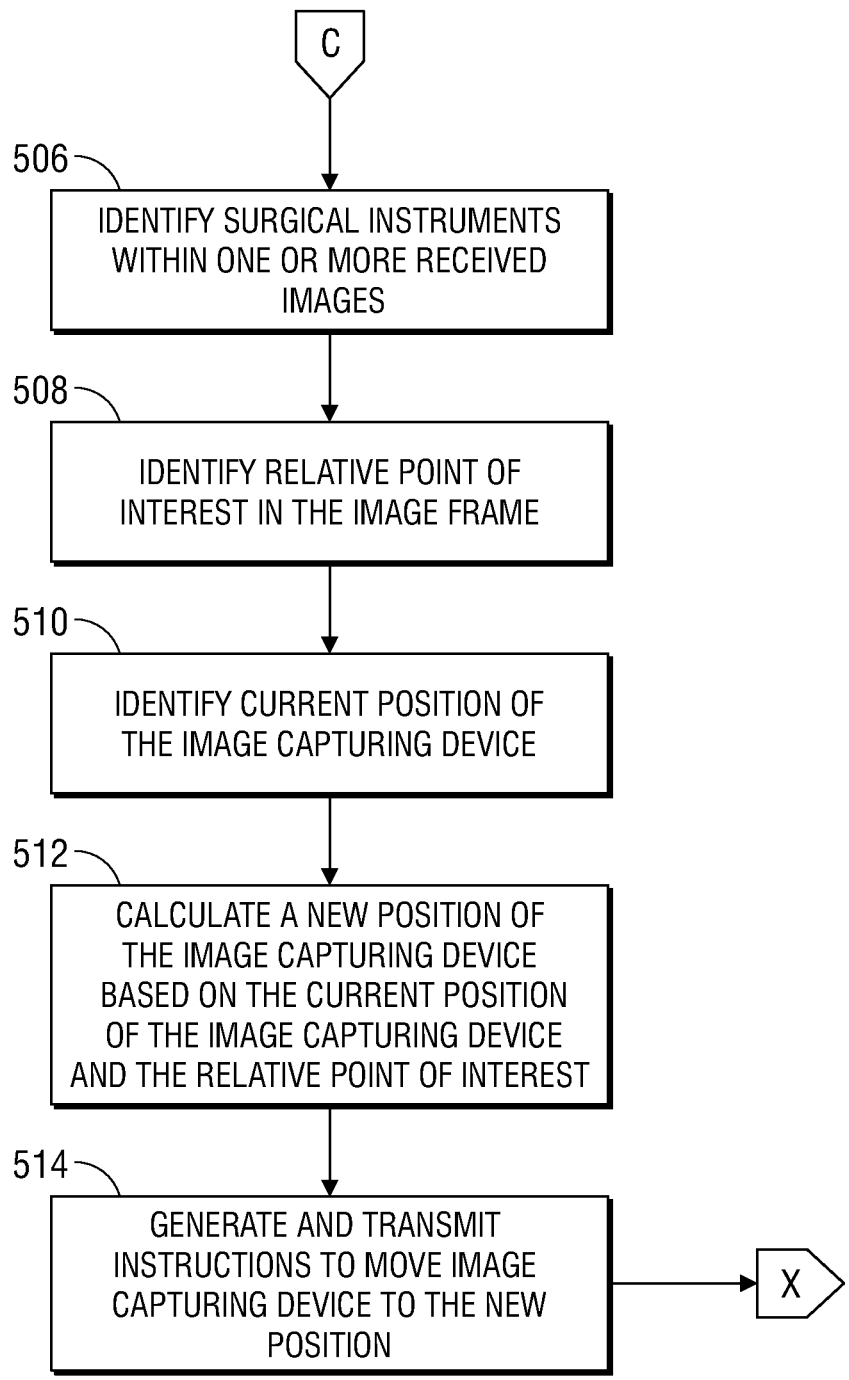
FIG. 5 is a flowchart that illustrates an exemplary method of employing the surgical robotic system of FIG. 1 to move the camera based on image processing.

Turning now to FIG. 5, an illustrative method 500 for moving an image capture device 196 in concurrent movement control mode based on image processing is shown. The computing device 180, in step 506, identifies one or more surgical instruments 195 or portions of surgical instruments 195 within one or more images received by the computing device 180. The computing device 180 receives one or more images captured by an image capture device 196 coupled to the robot arm of a robot assembly, such as robot assembly 190a or 190b. In some embodiments, the image capture device 196 is included within an endoscope. The one or more received images include one or more surgical instruments 195. The computing device 180 is configured with a multiple image processing techniques and algorithms, including image processing techniques to identify an object or a portion of an object within an image, such as surgical instruments 195 or portions of surgical instruments 195, for example, tips of the surgical instruments 195. In some embodiments, a second image capture device 196 is coupled to a different robot arm of a different robot assembly, and the computing device 180 receives images captured by the second image capture device 196. In some embodiments, the lens of the second image capture device 196 is positioned in a wide-angle view such that the captured images include the first image capture device 196 and the surgical instruments 195, and the computing device 180 is configured to identify surgical instruments 195 or portions of the surgical instruments 195 within the images received from the second image capture device 196.

In step 508, the computing device 180 identifies a relative point of interest in the image frame of each received images. As described above, the term "relative point of interest in an image frame" refers to particular position or point in an image frame relative to one or more surgical instruments 195 coupled to the robot assemblies of system 100. Examples of the relative point of interest include, but are not limited to, a center point of the tip of a surgical instrument, a center point between two or more surgical instrument tips, a centroid of two or more surgical instrument tips, a position that is offset from the center point or centroid of two or more surgical instrument tips. The computing device 180 calculates the relative point of interest within an image based on positions of the identified surgical instruments 195 or the surgical instrument tool tips. Therefore, as the surgical instruments 195 are moved within the patient, the relative point of interest calculated by the computing device 180 changes accordingly.

In step 510, the computing device 180 identifies the current position of the image capture device 196. In some embodiments, the computing device 180 is configured to save the most recent or current position of the image capture device 196 in a memory of the computing device 180 or a storage area operably coupled to the image computing device 180. In some embodiments, the computing device 180 receives data related to the position of the image capture device 196 after the image capture device 196 is moved to the position. The computing device 180 is configured to identify the current position of the image capture device 196 by accessing the storage area storing the most recently saved position of the image capture device 196.

In step 512, the computing device 180 calculates a new position of the image capture device 196 based on the current position of the image capture device 196 and the identified relative point of interest within the image. As described above, the relative point of interest changes based on the movement of the surgical instruments 195. Therefore, the position of the image capture device 196 is moved based in part on the movement of the surgical instruments 195. Thus, as the surgical instruments 195 are moved within the surgical site, the image capture device 196 follows the surgical instruments 195. In step 514, the computing device 180 generates instructions to the move the image capture device 196 to the new position and transmits the instructions to the robot assembly coupled to the image capture device 196. In some embodiments, various additional features may be applied to the image processing-based concurrent movement control mode that is described in connection with FIG. 5 in a manner similar to that described herein in connection with FIG. 3 for the handle motion-based concurrent movement control mode. Exemplary types of such features include, without limitation, filtering, velocity limiting, backlash/dead zone functionality, and/or the tying of motion of the image capture device 196 to a position of the handle 112 and/or to a mathematical combination of respective positions of multiple handles 112.

The phrases "in an example," "in examples," "in some examples," "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory described herein. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A method for camera control within a surgical robotic system, the method comprising:
   receiving data related to a movement of at least one handle among a plurality of handles of a surgeon console;
   determining a velocity of the movement of the at least one handle among the plurality of handles;
   comparing the determined velocity of the movement of the at least one handle among the plurality of handles with an expected velocity;
   calculating a new position of an image capture device based at least in part on the data related to the movement; and
   transmitting instructions to a first robot assembly coupled to the image capture device to move the image capture device to the new position.

2. The method of claim 1, wherein the data related to the movement of the at least one handle includes data related to a distance the at least one handle traveled, and the new position of the image capture device is calculated based at least in part on the data related to the distance the at least one handle traveled.

3. The method of claim 2, wherein the new position of the image capture device is calculated based at least in part on the data related to the distance the at least one handle traveled and a scaling factor applied to the distance the at least one handle traveled.

4. The method of claim 3, wherein the scaling factor applied to the distance is among a plurality of scaling factors, each scaling factor among the plurality of scaling factors associated with a direction of movement.

5. The method of claim 4, further comprising:
   selecting the scaling factor based at least on a direction the at least one handle traveled.

6. The method of claim 1, wherein the data related to the movement of the at least one handle includes data related to a direction the at least one handle traveled, and the new position of the image capture device is calculated based at least in part on the data related to the direction the at least one handle traveled.

7. The method of claim 6, wherein a direction of the new position of the image capture device relative to a current position of the image capture device is in the same direction as the direction the at least one handle traveled.

8. The method of claim 1, wherein the new position of the image capture device is calculated in response to a determination that the movement of the at least one handle is greater than a movement threshold value.

9. The method of claim 1, wherein the new position of the image capture device is calculated in response to a determination that the movement of the at least one handle is less than a sharp movement threshold value.

10. The method of claim 9, wherein whether the movement of the at least one handle is less than a sharp movement threshold value is determined using a Kalman filter.

11. The method of claim 9, wherein whether the movement of the at least one handle is less than a sharp movement threshold value is determined using a low pass filter.

12. A method for camera control within a surgical robotic system, the method comprising:
    receiving one or more images captured by an image capture device coupled to a robotic arm of a first robot assembly among a plurality of robot assemblies;
    identifying, within the one or more images, surgical instruments coupled to robotic arms of at least a subset of robot assemblies among the plurality of robot assemblies, different from the first robot assembly;
    identifying a relative point of interest based on the identified surgical instruments;
    calculating a new position of the image capture device based at least in part on the relative point of interest; and
    transmitting instructions to the first robot assembly to move the image capture device to the new position.

13. The method of claim 12, wherein the relative point of interest is a centroid calculated based on locations of the surgical instruments within the one or more images.

14. The method of claim 12, wherein the relative point of interest is a position offset from a center point calculated based on locations of the surgical instruments within the one or more images.

15. The method of claim 12, wherein the new position of the image capture device is calculated based at least in part on a current position of the image capture device and the relative point of interest.

16. The method of claim 12, further comprising:
receiving one or more images captured by a second image capture device coupled to a robotic arm of a second robot assembly among the plurality of robot assemblies, wherein the one or more images captured by the second image capture device include the surgical instruments and the image capture device is coupled to the first robot assembly;
identifying, within the one or more images captured by the second image capture device, the surgical instruments and the image capture device coupled to the first robot assembly;
identifying the relative point of interest based on the identified surgical instruments using the one or more images captured by the second image capture device;
calculating the new position of the image capture device based on the relative point of interest identified using the one or more images captured by the second image capture device; and
transmitting instructions to the first robot assembly to move the image capture device coupled to the first robot assembly to the new position.

17. The method of claim 16, wherein a zoom lens of the second image capture device is positioned in a wide angle view such that an image frame of the second image capture device includes the surgical instruments and the image capture device coupled to the first robot assembly.

* * * * *